(12) United States Patent
Evans et al.

(10) Patent No.: US 8,329,680 B2
(45) Date of Patent: *Dec. 11, 2012

(54) FORMULATION

(75) Inventors: John R Evans, Macclesfield (GB); Rosalind U Grundy, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 338 days.

This patent is subject to a terminal disclaimer.

(21) Appl. No.: 12/285,887

(22) Filed: Oct. 15, 2008

(65) Prior Publication Data

US 2010/0152149 A1    Jun. 17, 2010

Related U.S. Application Data

(63) Continuation of application No. 10/872,784, filed on Jun. 22, 2004, now Pat. No. 7,456,160.

(30) Foreign Application Priority Data

Jan. 10, 2000   (GB) .................................. 0000313.7
Apr. 12, 2000   (GB) .................................. 0008837.7

(51) Int. Cl.
*A61K 31/56*    (2006.01)

(52) U.S. Cl. ....................................... 514/177; 514/178

(58) Field of Classification Search .................. 514/177, 514/178
See application file for complete search history.

(56) References Cited

U.S. PATENT DOCUMENTS

| | | | |
|---|---|---|---|
| 2,822,316 A | 2/1958 | Richter et al. | |
| 2,983,649 A | 5/1961 | Ercoli et al. | |
| 3,164,520 A | 1/1965 | Huber | |
| 3,541,209 A | 11/1970 | Neumann et al. | |
| RE28,690 E | 1/1976 | Lehmann et al. | |
| 4,048,309 A | 9/1977 | Chen et al. | |
| 4,048,310 A | 9/1977 | Chen et al. | |
| 4,212,863 A | 7/1980 | Cornelius | |
| 4,388,307 A | 6/1983 | Cavanak | |
| 4,659,516 A | 4/1987 | Bowler et al. | |
| 4,888,331 A | 12/1989 | Elger et al. | |
| 5,095,129 A | 3/1992 | Ottow et al. | |
| 5,183,814 A | 2/1993 | Dukes | |
| 5,484,801 A | 1/1996 | Al-Razzak et al. | |
| 5,733,902 A | 3/1998 | Schneider | |
| 5,929,030 A | 7/1999 | Hamied et al. | |

(Continued)

FOREIGN PATENT DOCUMENTS

EP    0138504    4/1985

(Continued)

OTHER PUBLICATIONS

The abstract of Wakeling et al., The Journal of Steroid Biochemistry and Molecular Biology, 1992;43:1-3:173-177.*

(Continued)

*Primary Examiner* — San-Ming Hui
(74) *Attorney, Agent, or Firm* — Finnegan, Henderson, Farabow, Garrett & Dunner LLP

(57) ABSTRACT

The invention relates to a novel sustained release pharmaceutical formulation adapted for administration by injection containing the compound 7α-[9-(4,4,5,5,5-pentafluoropentylsulphinyl)nonyl]oestra-1,3,5(10)-triene-3,17β-diol, more particularly to a formulation adapted for administration by injection containing the compound 7α-[9-(4,4,5,5,5-pentafluoropentylsulphinyl)nonyl]oestra-1,3,5(10)-triene-3, 17β-diol in solution in a ricinoleate vehicle which additionally comprises at least one alcohol and a non-aqueous ester solvent which is miscible in the ricinoleate vehicle.

20 Claims, 2 Drawing Sheets

U.S. PATENT DOCUMENTS

2001/0006963 A1    7/2001    Lachnit-Fixson et al.

FOREIGN PATENT DOCUMENTS

| | | |
|---|---|---|
| EP | 0310542 A1 | 4/1989 |
| EP | 0346014 | 12/1989 |
| EP | 0819431 | 3/1999 |
| EP | 0905143 | 3/1999 |
| FR | 6241 | 9/1968 |
| GB | 817241 | 7/1959 |
| GB | 1126892 | 9/1968 |
| GB | 1207571 | 10/1970 |
| GB | 1569286 | 6/1980 |
| JP | 43-27327 | 11/1992 |
| JP | 09-208496 | 12/1997 |
| JP | 10-203982 | 4/1998 |
| JP | 10-152438 | 6/1998 |
| JP | 11-501649 | 2/1999 |
| JP | 11-158200 | 6/1999 |
| SU | 549118 | 3/1977 |
| SU | 676284 | 7/1979 |
| WO | WO 95/12383 | 5/1995 |
| WO | WO 96/19997 | 7/1996 |
| WO | WO 97/21440 | 6/1997 |
| WO | WO 97/37653 | 10/1997 |
| WO | WO 97/40823 | 11/1997 |
| WO | WO 98/11902 | 3/1998 |
| WO | WO 99/27906 | 6/1999 |
| WO | WO 03/006064 | 1/2003 |
| WO | WO 2011/012885 | 2/2011 |
| ZA | 681014 | 2/1968 |
| ZA | 682530 | 4/1968 |

OTHER PUBLICATIONS

Anschel, "Lösungsmittel und Lösungsvermittler in Injektionen", Pharm, Ind., 1965, vol. 27 (11a), pp. 781-787.

Davis et al., "17-Alpha-Hydroxyprogesterone-Caproate: . . . with Chemically Pure Progesterone", J. Clin. Endocrinol. and Metabolism, 1955, vol. 15, pp. 923-930.

Dukes et al., "Antiuterotrophic effects of pure antioestrogen. ICI 182,780, . . . the uterus in ovariectomized monkeys", J. Endocrinology, 1992, vol. 135, pp. 239-247.

Dukes et al., "Antiuterotrophic effects of the pure antioestrogen ICI 182, 780 . . . quantitative magnetic resonance imaging"; J. Endocrinology, 1992, vol. 138, pp. 203-209.

Howell et al., "Pharmacokinetics, pharmacological and anti-tumour effects of the specific anti-oestrogen ICI 182780 in women with advanced breast cancer", British Journal of Cancer, 1996, vol. 74, pp. 300-308.

Howell et al., "Response to a specific antioestrogen (ICI 182780) in tamoxifen-resistant breast cancer", The Lancet, Jan. 7, 1995, pp. 29-30.

Mackey et al, "Tolerability of intramuscular injections of testosterone ester in oil vehicle", Human Reproduction, vol. 10, No. 4, pp. 869-865, 1995.

Martindale, 32nd Ed., "Alcohol", Pharmaceutical Press, 1999, pp. 1099-1101.

Martindale, 32nd Ed., "Benzoates" and "Benzyl Alcohol"; Pharmaceutical Press, 1999, pp. 1102-1104.

Martindale, 32nd Ed., "Caster Oil"; 32nd Ed., Pharmaceutical Press, 1999, p. 1560.

Migally, "Effect of Castor Oil and Benzyl Benzoate Used as a Vehicle for Antiandrogens on the Adrenal Cortex", Archives of Andrology 2, 1979 pp. 365-369.

Osborne et al., "Comparison of the Effects of a Pure Steroidal Antiestrogen With Those of Tamoxifen in a Model of Human Breast Cancer", Journal of the National Cancer, May 1995, vol. 87, No. 10, pp. 746-750.

Pellegrino, "Use of 17 α Hydroxyprogesterone Caproate in Threatened Abortion", Current Therapeutic Research, vol. 4, No. 6, Jun. 1962, pp. 301-305.

Piver et al., "Medroxyprogesterone Acetate (Depo-Provera) vs . . . Women with Metastatic Endometrial Adenocarcinoma", Cancer, vol. 45, American Cancer Society, 1980, pp. 268-272.

Remington's Pharmaceutical Sciences, 18th ed., 1990, p. 219.

Riffkin et al., "Castor Oil as a Vehicle for Parenteral Administration of Steroid Hormones", Journal of Pharmaceutical Sciences, vol. 53, No. 8, Aug. 1964, pp. 891-895.

Robertson et al., "A partially-blind, randomised, multicentre study comparing the anti-tumor effects of single doses (50, 125 and 250mg) of long-acting (LA) 'faslodex' (ICI 182,780 with tamoxifen in postmenopausal women with primary breast cancer prior to surgery"; Abstract 28, 22nd Annual San Antonio Breast Cancer Symposium: Dec. 8-11, 1999, San Antonio, Breast Cancer Research and Treatment 1999; 57 (1; special issue); p. 31.

Sawada et al., "Estrogen Receptor Antagonist ICII82,780 Exacerbates Ischemic Injury in Female Mouse", Journal of Cerebral Blood Flow and Metabolism, vol. 20. No. 1, 2000, pp. 112-118.

Vidal, Le Dictionnaire, "Benzo-Gynoestryl Retard", 1998 p. 201.

Vidal, Le Dictionnaire, "Gravibinan", 1995, pp. 660-661.

Vidal, Le Dictionnaire, "Parabolan", 1997, p. 1245.

Vidal, Le Dictionnaire, "Trophobolene", 1997, pp. 1706-1707.

Wakeling et al., "A Potent Specific Pure Antiestrogen with Clinical Potential", Cancer Research, 1991, vol. 51, pp. 3867-3873.

Waterton et al., "A Case of Adenomyosis in a Pigtailed Monkey . . . Treated with the Novel Pure Antiestrogen, ICI 182,780"; Laboratory Animal Science, 1993, vol. 43, No. 3, 1993, pp. 247-251.

"Pharmaceutical dosage forms: Parenteral medications, vol. 1", 2nd edition, edited by Avis, Lieberman and Lachman, 1992.

The Merck Index, 12th Ed., Merck & Co., Inc., pp. xiv, 189-190, 641-642 and 1715 (1996).

Guerrini, et al., "Pharmacokinetics of probenecid in sheep", J Vet Pharmacol Ther., 128-135 (1985).

Lavy, et al., "Pharmacokinetics of clindamycin HCl administered intravenously, intramuscularly and subcutaneously to dogs", J Vet Pharmacol Ther., 22(4):261-265 (1999).

Ismail, "Disposition kinetics of difloxacin after intravenous, intramuscular and subcutaneous administration in calves", Vet Res Commun., 31(4):467-476 (2007).

Documents from the prosecution of European Application No. 01900186.6 (EP 1 250 138) from Aug. 27, 2009 to Dec. 15, 2011.

Documents from the prosecution of European Application No. 10180667.7 (EP 2 266 573) from Nov. 23, 2010 to Dec. 19, 2011.

Documents from the prosecution of European Application No. 10180661.0 (EP 2 286 818) from Jan. 19, 2011 to Dec. 19, 2011.

Declaration Under 35 U.S.C § 1.132 of Dr. Paul Gellert filed in Aug. 2008 in U.S. Appl. No. 10/872,784.

McLeskey et al., "Tamoxifen-resistant fibroblast growth factor-transfected MCF-7 cells are cross-resistant in vivo to the antiestrogen ICI 182,780 and two aromatase inhibitors," Clin. Cancer Res., 4:697-711 (1998).

JRF Robertson, et al., "Fulvestrant: pharmacokinetics and pharmacology," British Journal of Cancer, 90(1):S7-S10 (2004).

John F. R. Robertson, "Fulvestrant (Faslodex®)—how to make a good drug better," The Oncologist, 12:774-784 (2007).

Search Report for European Patent Application No. 10180667.7 dated Nov. 23, 2010.

Search Report for European Patent Application No. 10180661.0 dated Jan. 19, 2011.

Documents from the Opposition against European Patent Application No. 01900186.6 from Apr. 21, 2009 to Sep. 7, 2009.

P.K. Gupta and G.A. Brazeau (eds). *Injectable Drug Development: Techniques to Reduce Pain and Irritation.* Chapters 11 & 17 Interpharm Press, Denver, Colorado (1999).

P.V. Lopatin, V. P. Safonov, T. P. Litvinova and L. M. Yakimenko. Use of nonaqueous solvents to prepare injection solutions. *Pharm. Chem. J.* 6:724-733 (1972).

S. Nema, R.J. Washkuhn, and R.J. Brendel. Excipients and their use in injectable products. *PDA J. Pharm. Sci. Technol.* 51:166-71 (1997).

*Physicians' Desk Reference* (*27th edition*). 1277-1278, 1350-1354, 1391-1392 Medical Economics Company, Oradell, NJ (1973).

M. F. Powell, T. Nguyen, and L. Baloian. Compendium of excipients for parenteral formulations. *PDA J. Pharm. Sci. Technol.* 52:238-311 [pp. 238-255 provided] (1998).

R. G. Strickley. Parenteral formulations of small molecule therapeutics marketed in the United States (1999)—Part I. *PDA J Pharm. Sci. Technol*. 53:324-349 (1999).

R. G. Strickley. Parenteral formulations of small molecule therapeutics marketed in the United States (1999)—Part II *PDA J Pharm. Sci. Technol*. 54:69-96 (2000).

R. G. Strickley. Parenteral formulations of small molecule therapeutics marketed in the United States (1999)—Part III. *PDA J Pharm. Sci. Technol*. 54:152-169 (2000).

Y.C. J. Wang and R. R. Kowal. Review of excipients and pH's for parenteral products used in the United States. *J Parenteral Drug Assoc*. 34:452-462 (1980).

U.S. Appl. No. 13/387,584, filed Jan. 27, 2012, Dimery et al.

Buzdar, A. U., "Fulvestrant—A novel estrogen receptor antagonist for the treatment of advanced breast cancer," *Drugs of Today*, 44(9):679-692 (2008).

"Comparison of fulvestrant (faslodex) 250 mg and 500 mg in postmenopausal women with estrogen receptor-positive advanced breast cancer progressing or relapsing after previous endocrine therapy," Clinicaltrials.gov (May 20, 2009) retrieved Jan. 24, 2012.

Di Leo A., et al., "Confirm: a phase III, randomized, parallel-group trial comparing fulvestrant 250 mg vs fulvestrant 500 mg in postmenopausal women with estrogen receptor-positive advanced breast cancer," Cancer Res., 69(24) Supp. 3, (2009).

International Search Report for PCT Application No. PCT/GB10/51228 (WO 2011/012885) mailed Dec. 20, 2012.

International Preliminary Report on Patentability for PCT Application No. PCT/GB10/51228 (WO 2011/012885) mailed Dec. 20, 2012.

Documents from the prosecution of European Application No. 01900186.6 (EP 1 250 138) dated Dec. 15, 2011.

Documents from the prosecution of European Application No. 01900186.6 (EP 1 250 138) dated Feb. 27, 2012.

* cited by examiner

FLOW DIAGRAM OF MANUFACTURING

Ingredients/Components

- Fulvestrant
- Alcohol
- Benzyl Alcohol

→ STAGE 1: DISSOLUTION OF ACTIVE AGENT

↓

- Benzyl Benzoate

→ STAGE 2: MIX

↓

- Castor Oil

→ STAGE 3: MAKE TO WEIGHT

↓

STAGE 4: STERILE FILTRATION (0.2μm) INTO BULK RECEIVING VESSEL

↓

STAGE 5: STERILE (0.2μm) IN-LINE FILTRATION

↓

STAGE 6: ASEPTIC FILLING, AND STOPPERING

↓

STAGE 7: VISUAL INSPECTION

Figure 2

FORMULATION

CROSS-REFERENCE TO RELATED APPLICATIONS

This application is a Continuation Application of U.S. patent application Ser. No. 10/872,784, filed Jun. 22, 2004, now U.S. Pat. No. 7,456,160 which claims benefit of U.S. patent application Ser. No. 09/756,291, filed Jan. 9, 2001 which claims the benefit of Great Britain Application No. 0008837.7 filed Apr. 12, 2000 and Great Britain Application No. 0000313.7, filed Jan. 10, 2000, all of which are incorporated herein by reference in their entireties.

BACKGROUND OF THE INVENTION

1. Field of the Invention

The invention relates to a novel sustained release pharmaceutical formulation adapted for administration by injection containing the compound 7α-[9-(4,4,5,5,5-pentafluoropentylsulphinyl)nonyl]oestra-1,3,5(10)-triene-3,17β-diol.

2. Description of the Related Art

Oestrogen deprivation is fundamental to the treatment of many benign and malignant diseases of the breast and reproductive tract. In premenopausal women, this is achieved by the ablation of ovarian function through surgical, radiotherapeutic, or medical means, and, in postmenopausal women, by the use of aromatase inhibitors.

An alternative approach to oestrogen withdrawal is to antagonise oestrogens with antioestrogens. These are drugs that bind to and compete for oestrogen receptors (ER) present in the nuclei of oestrogen-responsive tissue. Conventional nonsteroidal antioestrogens, such as tamoxifen, compete efficiently for ER binding but their effectiveness is often limited by the partial agonism they display, which results in an incomplete blockade of oestrogen-mediated activity (Farr and Jordan 1984, May and Westley 1987).

The potential for nonsteroidal antioestrogens to display agonistic properties prompted the search for novel compounds that would bind ER with high affinity without activating any of the normal transcriptional hormone responses and consequent manifestations of oestrogens. Such molecules would be "pure" antioestrogens, clearly distinguished from tamoxifen-like ligands and capable of eliciting complete ablation of the trophic effects of oestrogens. Such compounds are referred to as Estrogen Receptor-Downregulators (E.R.D.). The rationale for the design and testing of novel, pure antioestrogens has been described in: Bowler et al 1989, Wakeling 1990a, 1990b, 1990c. Wakeling and Bowler 1987, 1988.

Steroidal analogues of oestradiol, with an alkylsulphinyl side chain in the 7α position, provided the first examples of compounds devoid of oestrogenic activity (Bowler et al 1989). One of these, 7α-[9-(4,4,5,5,5-pentafluoropentyl sulphinyl)nonyl]oestra-1,3,5-(10)triene-3,17β-diol was selected for intensive study on the basis of its pure oestrogen antagonist activity and significantly increased antioestrogenic potency over other available antioestrogens. In vitro findings and early clinical experience with 7α-[9-(4,4,5,5,5-pentafluoropentylsulphinyl)nonyl]oestra-1,3-5(10)-triene-3,17β-diol have promoted interest in the development of the drug as a therapeutic agent for oestrogen-dependent indications such as breast cancer and certain benign gynaecological conditions.

7α-[9-(4,4,5,5,5-Pentafluoropentylsulphinyl)nonyl]oestra-1,3-5(10)-triene-3,17β-diol, or ICI 182,780, has been allocated the international non-proprietary name fulvestrant, which is used hereinafter. When referring to fulvestrant we include pharmaceutically-acceptable salts thereof and any possible solvates of either thereof.

Fulvestrant binds to ER with an affinity similar to that of oestradiol and completely blocks the growth stimulatory action of oestradiol on human breast cancer cells in vitro; it is more potent and more effective than tamoxifen in this respect. Fulvestrant blocks completely the uterotrophic action of oestradiol in rats, mice and monkeys, and also blocks the uterotrophic activity of tamoxifen.

Because fulvestrant has none of the oestrogen-like stimulatory activity that is characteristic of clinically available antioestrogens such as tamoxifen or toremifene, it may offer improved therapeutic activity characterised by more rapid, complete, or longer-lasting tumour regression; a lower incidence or rate of development of resistance to treatment; and a reduction of tumour invasiveness.

In intact adult rats, fulvestrant achieves maximum regression of the uterus at a dose which does not adversely affect bone density or lead to increased gonadotrophin secretion. If also true in humans, these findings could be of extreme importance clinically. Reduced bone density limits the duration of oestrogen-ablative treatment for endometriosis. Fulvestrant does not block hypothalamic ER. Oestrogen ablation also causes or exacerbates hot flushes and other menopausal symptoms; fulvestrant will not cause such effects because it does not cross the blood-brain barrier.

European Patent Application No. 0 138 504 discloses that certain steroid derivatives are effective antioestrogenic agents. The disclosure includes information relating to the preparation of the steroid derivatives. In particular there is the disclosure within Example 35 of the compound 7α-[9-(4,4,5,5,5-pentafluoropentylsulphinyl)nonyl]oestra-1,3,5(10)-triene-3,17β-diol, which compound is specifically named in claim 4. It is also disclosed that the compounds of that invention may be provided for use in the form of a pharmaceutical composition comprising a steroid derivative of the invention together with a pharmaceutically-acceptable diluent or carrier. It is stated therein that the composition can be in a form suitable for oral or parenteral administration.

Fulvestrant shows, along with other steroidal based compounds, certain physical properties which make formulation of these compounds difficult. Fulvestrant is a particularly lipophilic molecule, even when compared with other steroidal compounds, and its aqueous solubility is extremely low at around 10 ngml$^{-1}$ (this is an estimate from a water/solvent mixture solute since measurements this low could not be achieved in a water only solute).

Currently there are a number of sustained release injectable steroidal formulations which have been commercialised. Commonly these formulations use oil as a solvent and wherein additional excipients may be present. Below in Table 1 are described a few commercialised sustained release injectable formulations.

In the formulations within Table 1 a number of different oils are used to solubilise the compound and additional excipients such as benzyl benzoate, benzyl alcohol and ethanol have been used. Volumes of oil needed to solubilise the steroid active ingredient are low. Extended release is achievable for periods from 1 to 8 weeks.

TABLE 1

OIL BASED LONG-ACTING INTRAMUSCULAR INJECTIONS

| PRODUCT NAME | STEROID | DOSE | TYPE | COMP'. | SOURCE | OIL | BzBz |
|---|---|---|---|---|---|---|---|
| SUSTANON 100 | Testosterone proprionate | 30 mg | Androgen | Organon | ABPI Data Sheet Comp. 1999 | Arachis | |
| | Testosterone phenylproprionate | 60 mg | | | | | |
| | Testosterone isocaproate | 60 mg | | | | | |
| | Testosterone decanoate | 100 mg | | | | | |
| PROLUTON DEPOT | Hydroxy progesterone hexanoate | 250 mgml$^{-1}$ | Progestogen | Schering HC | ABPI Data Sheet Comp. 1999 | Castor | up to 46% |
| TOCOGESTAN | Hydroxy progesterone enantate | 200 mg | Progestogen | Theramax | Dict. Vidal 1999 | Ethyl oleate | *40% |
| | Progesterone | 50 mg | | | | | |
| | α-Tocopherol | 250 mg | | | | | |
| TROPHOBOLENE | Estrapronicate | 1.3 mg | Mixed | Theramax | Dict. Vidal 1997 | Olive | 45% |
| | Nandrolone undecanoate | 50 mg | | | | | |
| | Hydroxyprogesterone heptanoate | 80 mg | | | | | |
| NORISTERAT | Norethisterone oenanthoate | 200 mg | Contraceptive | Schering HC | ABPI Data Sheet Comp. 1999 | Castor | YES |
| BENZO-GYNOESTRYL | Estradiol hexahydrobenzoate | 5 mg | Estradiol | Roussel | Dict. Vidal 1998 | Arachis | |
| PROGESTERONE-RETARD | Hydroxy progesterone caproate | 250 mgml$^{-1}$ | Progestogen | Pharlon | Dict. Vidal 1999 | Castor | YES |
| GRAVIBINAN | Estradiol 17-β-valerate | 5 mgml$^{-1}$ | Mixed | Schering HC | Dict. Vidal 1995 | Castor | YES |
| | Hydroxyprogesterone caproate | 250 mgml$^{-1}$ | | | | | |
| PARABOLAN | Trenbolone | 76 mg | Androgen | Negma | Dict. Vidal 1997 | Arachis | |
| DELESTROGEN | Estradiol valerate | 20 mgml$^{-1}$ 40 mgml$^{-1}$ | Estradiol | BMS | J. Pharm. Sci (1964) 53(8) 891 | Castor | 78% 58% |
| DELALUTIN | 17-Hydroxy progesterone | 250 mgml$^{-1}$ | Progestrogen | DMS | J. Pharm. Sci. (1964) 53(8) 891 | Castor | YES |

| PRODUCT NAME | STEROID | BzOH | EtOH | DOSE | DOSING |
|---|---|---|---|---|---|
| SUSTANON 100 | Testosterone proprionate Testosterone phenylproprionate Testosterone isocaproate Testosterone decanoate | 0.1 ml | | 1 ml | 3 weeks |
| PROLUTON DEPOT | Hydroxy progesterone hexanoate | | | 1 or 2 ml | 1 week |
| TOCOGESTAN | Hydroxy progesterone enantate Progesterone α-Tocopherol | | | 2 ml | <1 week |
| TROPHOBOLENE | Estrapronicate Nandrolone undecanoate Hydroxyprogesterone heptanoate | | | 1 ml | 15 to 30 days |
| NORISTERAT | Norethisterone oenanthoate | | | 1 ml | 8 weeks |
| BENZO-GYNOESTRYL | Estradiol hexahydrobenzoate | | | 1 ml | 1 week |
| PROGESTERONE-RETARD | Hydroxy progesterone caproate | | | 1 or 2 ml | 1 week |
| GRAVIBINAN | Estradiol 17-β-valerate Hydroxyprogesterone caproate | | | 1 or 2 ml | 1-2 weeks |
| PARABOLAN | Trenbolone | 75 mg | 45 mg | 1.5 ml | 2 weeks |
| DELESTROGEN | Estradiol valerate | 20% 40% | 2% 2% | | |
| DELALUTIN | 17-Hydroxy progesterone | YES | up to 2% | | |

BzBz = benzylbenzoate
BzOH = benzylalcohol
EtOH = ethanol
Dict. Vidal = Dictionnaire Vidal
% are w/v and
*approximate as measured directly from a single sample described which comprises 50 mg of fulvestrant, 400 mg of benzyl alcohol and sufficient castor oil to bring the solution to a volume of 1 ml. Manufacture at a commercial scale of a formulation as described in U.S. Pat. No. 5,183,814 will be complicated by the high alcohol concentration. Therefore, there is a need to lower the alcohol concentration in fulvestrant formulations whilst preventing precipitation of fulvestrant from the formulation.

SUMMARY OF THE INVENTION

The invention relates to a novel sustained release pharmaceutical formulation adapted for administration by injection containing the compound 7α-[9-(4,4,5,5,5-pentafluoropentylsulphinyl)nonyl]oestra-1,3,5(10)-triene-3,17β-diol, more particularly to a formulation adapted for administration by injection containing the compound 7α-[9-(4,4,5,5,5-pentafluoropentylsulphinyl)nonyl]oestra-1,3,5(10)-triene-3, 17β-diol in solution in a ricinoleate vehicle which additionally comprises at least one alcohol and a non-aqueous ester solvent which is miscible in the ricinoleate vehicle.

BRIEF DESCRIPTION OF THE DRAWING

FIG. 2 shows a process flow diagram associated with the Formulation Example.

DETAILED DESCRIPTION OF THE INVENTION

Figure 1:
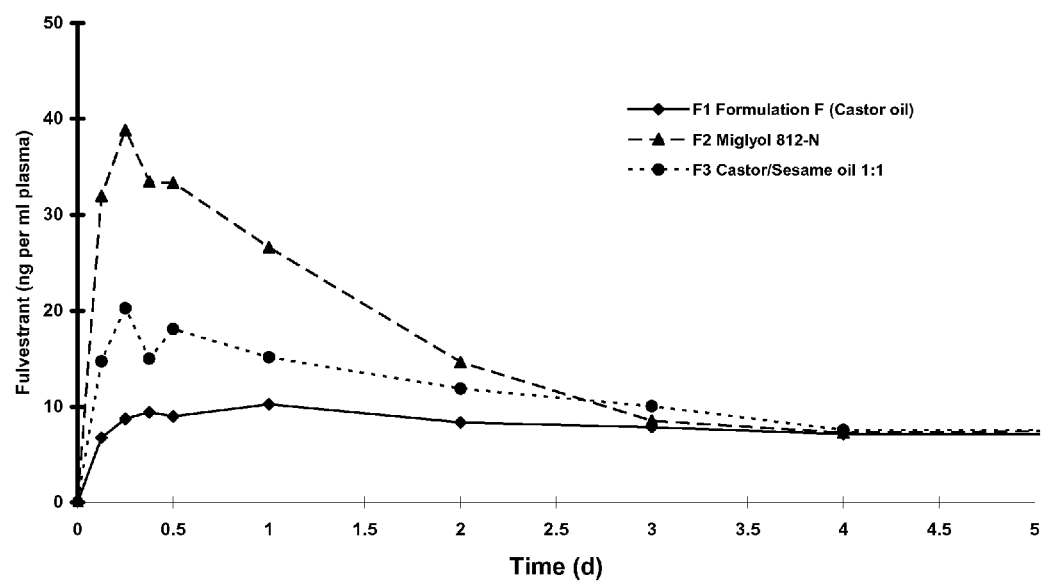
FIG. 1 shows the release profile in vivo of the four formulations from the second part of Table 4 below, and shows the effect of the fixed oil component on fulvestrant plasma profile over five days following intramuscular administration in rabbits.

Table 2 shows the solubility of fulvestrant in a number of different solvents.

TABLE 2

SOLUBILITY OF FULVESTRANT

| SOLVENT | SOLUBILITY (mgml$^{-1}$ at 25° C.) |
|---|---|
| Water | 0.001 |
| Arachis oil | 0.45 |
| Sesame oil | 0.58 |
| Castor oil | 20 |
| Miglyol 810 | 3.06 |
| Miglyol 812 | 2.72 |
| Ethyl oleate | 1.25 |
| Benzyl benzoate | 6.15 |
| Isopropyl myristate | 0.80 |
| Span 85 (surfactant) | 3.79 |
| Ethanol | >200 |
| Benzyl Alcohol | >200 |

As can be seen fulvestrant is significantly more soluble in castor oil than any of the other oils tested. The greater solvating ability of castor oil for steroidal compounds is known and is attributed to the high number of hydroxy groups of ricinoleic acid, which is the major constituent of the fatty acids within the triglycerides present in castor oil—see (Riffkin et. al. J. Pharm. Sci., (1964), 53, 891).

However, even when using the best oil based solvent, castor oil, we have found that it is not possible to dissolve fulvestrant in an oil based solvent alone so as to achieve a high enough concentration to dose a patient in a low volume injection and achieve a therapeutically significant release rate. To achieve a therapeutically significant release rate the amount of fulvestrant needed would require the formulation volume to be large, at least 10 ml. This requires the doctor to inject an excessively large volume of formulation to administer a dose significantly high enough for human therapy.

Currently guidelines recommend that no more than 5 mls of liquid is injected intramuscularly in a single injection. Pharmacologically active doses required for a 1 month long acting depot formulation of fulvestrant is around 250 mg. Therefore, when dissolved in just castor oil, fulvestrant would need to be administered in at least 10 ml of castor oil.

The addition of organic solvents in which fulvestrant is freely soluble, and which are miscible with castor oil, may be used, such as an alcohol. With the addition of high concentrations of an alcohol concentrations of >50 mgml$^{-1}$ of fulvestrant in a castor oil formulation is achievable, thereby giving an injection volumes of <5 ml—see Table 3 below. We have surprisingly found that the introduction of a non-aqueous ester solvent which is miscible in the castor oil and an alcohol surprisingly eases the solubilisation of fulvestrant into a concentration of at least 50 mgml$^{-1}$—see Table 3 below. The finding is surprising since the solubility of fulvestrant in non-aqueous ester solvents—see Table 2 above—is significantly lower than the solubility of fulvestrant in an alcohol. The solubility of fulvestrant is also lower in non-aqueous ester solvents than is the solubility of fulvestrant in castor oil.

Therefore, we present as a feature of the invention a pharmaceutical formulation comprising fulvestrant (preferably fulvestrant is present at 3-10% w/v, 4-9% w/v, 4-8% w/v, 4-7% w/v, 4-6% w/v and most preferably at about 5% w/v) in a ricinoleate vehicle, a pharmaceutically acceptable non-aqueous ester solvent, and a pharmaceutically acceptable alcohol wherein the formulation is adapted for intramuscular administration and attaining a therapeutically significant blood plasma fulvestrant concentration for at least 2 weeks.

Another feature of the invention is a pharmaceutical formulation comprising fulvestrant in which the formulation is adapted for intra-muscular injection into a human and which is capable after injection of attaining a therapeutically significant blood plasma fulvestrant concentration for at least 2 weeks.

Further features of the invention include a pharmaceutical formulation adapted for intra-muscular injection comprising fulvestrant, 30% or less weight of a pharmaceutically-acceptable alcohol per volume of formulation, at least 1% weight of a pharmaceutically-acceptable non-aqueous ester solvent miscible in a ricinoleate vehicle per volume of formulation and a sufficient amount of a ricinoleate vehicle so as to prepare a formulation which is capable after injection of attaining a therapeutically significant blood plasma fulvestrant concentration for at least 2 weeks.

Further features of the invention include a pharmaceutical formulation adapted for intra-muscular injection comprising fulvestrant; 35% (preferably 30% and ideally 25%) or less weight of a pharmaceutically-acceptable alcohol per volume of formulation, at least 1% (preferably at least 5% or ideally 10%) weight of a pharmaceutically-acceptable non-aqueous ester solvent miscible within a ricinoleate vehicle per volume of formulation and a sufficient amount of a ricinoleate vehicle so as to prepare a formulation of at least 45 mgml$^{-1}$ of fulvestrant.

For the avoidance of any doubt when using the term % weight per volume of formulation for the constituents of the formulation we mean that within a unit volume of the formulation a certain percentage of the constituent by weight will be present, for example a 1% weight per volume formulation will contain within a 100 ml volume of formulation 1 g of the constituent. By way of further illustration

| % of x by weight per volume of formulation | weight of x in 1 ml of formulation |
|---|---|
| 30% | 300 mg |
| 20% | 200 mg |

-continued

| % of x by weight per volume of formulation | weight of x in 1 ml of formulation |
|---|---|
| 10% | 100 mg |
| 5% | 50 mg |
| 1% | 10 mg |

Preferred pharmaceutical formulations of the invention are as described above wherein:
1. The total volume of the formulation is 6 ml, or less, and the concentration of fulvestrant is at least 45 mgml$^{-1}$.
2. The total amount of fulvestrant in the formulation is 250 mg, or more, and the total volume of the formulation is 6 ml, or less.
3. The total amount of fulvestrant in the formulation is 250 mg and the total volume of the formulation is 5-5.25 ml.

It is appreciated that in the formulation an excess of formulation may be included to allow the attendant physician or care giver to be able to deliver the required dose. Therefore, when a 5 ml dose is required it would be appreciated that an excess of up to 0.25 ml, preferably up to 0.15 ml will also be present in the formulation. Typically the formulation will be presented in a vial or a prefilled syringe, preferably a prefilled syringe, containing a unit dosage of the formulation as described herein, these being further features of the invention.

Preferred concentrations of a pharmaceutically-acceptable alcohol present in any of the above formulations are; at least 3% w/v, at least 5% w/v, at least 7% w/v, at least 10% w/v, at least 11% w/v, at least 12% w/v, at least 13% w/v, at least 14% w/v, at least 15% w/v and, preferably, at least 16% w/v. Preferred maximal concentrations of pharmaceutically-acceptable alcohol present in the formulation are 28% w/v or less, 22% w/v or less and 20% w/v or less. Preferred ranges of pharmaceutically-acceptable alcohol present in any of the above formulations are selected from any minimum or maximum value described above and 3-35% w/v, 4-35% w/v, 5-35% w/v, 5-32% w/v, 7-32% w/v, 10-30% w/v, 12-28% w/v, 15-25% w/v, 17-23% w/v, 18-22% w/v and ideally 19-21% w/v.

The pharmaceutically-acceptable alcohol may consist of one alcohol or a mixture of two or more alcohols, preferably a mixture of two alcohols. Preferred pharmaceutically-acceptable alcohols for parenteral administration are ethanol, benzyl alcohol or a mixture of both ethanol and benzyl alcohol, preferably the ethanol and benzyl alcohol are present in the formulation in the same w/v amounts. Preferably the formulation alcohol contains 10% w/v ethanol and 10% w/v benzyl alcohol.

The pharmaceutically-acceptable non-aqueous ester solvent may consist of one or a mixture of two or more pharmaceutically-acceptable non-aqueous ester solvents, preferably just one. A preferred pharmaceutically-acceptable non-aqueous ester solvent for parenteral administration is selected from benzyl benzoate, ethyl oleate, isopropyl myristate, isopropyl palmitate or a mixture of any thereof.

The ricinoleate vehicle should preferably be present in the formulation in a proportion of at least 30% weight per volume of the formulation, ideally at least 40% or at least 50% weight per volume of formulation.

It will be understood by the skilled person that the pharmaceutically-acceptable alcohol will be of a quality such that it will meet pharmacopoeial standards (such as are described in the US, British, European and Japanese pharmacopoeias) and as such will contain some water and possibly other organic solvents, for example ethanol in the US Pharmacopeia contains not less than 94.9% by volume and not more than 96.0% by volume of ethanol when measured at 15.56° C. Dehydrated alcohol in the US Pharmacopeia contains not less than 99.5% ethanol by volume when measured at 15.56° C.

Preferred concentrations of the pharmaceutically-acceptable non-aqueous ester solvent present in any of the above formulations are; at least 5% w/v, at least 8% w/v, at least 10% w/v, at least 11% w/v, at least 12% w/v, at least 13% w/v, at least 15% w/v, at least 16% w/v, at least 17% w/v, at least 18% w/v, at least 19% w/v and at least 20% w/v. Preferred maximal concentrations of the pharmaceutically-acceptable non-aqueous ester solvent are; 60% w/v or less, 50% w/v or less, 45% w/v or less, 40% w/v or less, 35% w/v or less, 30% w/v or less and 25% w/v or less. A preferred concentration is 15% w/v. Preferred ranges of pharmaceutically-acceptable non-aqueous ester solvent present in any of the above formulations are selected from any minimum or maximum value described above and preferably are; 5-60% w/v, 7-55% w/v, 8-50% w/v, 10-50% w/v, 10-45% w/v, 10-40% w/v, 10-35% w/v, 10-30% w/v, 10-25% w/v, 10-25% w/v, 12-25% w/v, 12-22% w/v, 12-20% w/v, 12-18% w/v, 13-17% w/v and ideally 14-16% w/v. Preferably the ester solvent is benzyl benzoate, most preferably at about 15% w/v.

It will be understood by the skilled person that the pharmaceutically-acceptable non-aqueous ester solvent will be of a quality that it will meet pharmacopoeial standards (such as described in the US, British, European and Japanese pharmacopoeias).

Preferred combinations of pharmaceutically-acceptable alcohol and pharmaceutically-acceptable non-aqueous ester solvent in the formulation are set out below:

| Pharmaceutically-acceptable alcohol(% w/v) | Pharmaceutically-acceptable non-aqueous ester (% w/v) |
|---|---|
| 10-30 | 5-60, 7-55, 8-50, 10-50, 10-45, 10-40, 10-35, 10-30, 10-25, 12-25, 12-22, 12-20, 12-18, 13-17 and ideally 14-16. |
| 17-23 | 5-60, 7-55, 8-50, 10-50, 10-45, 10-40, 10-35, 10-30, 10-25, 12-25, 12-22, 12-20, 12-18, 13-17 and ideally 14-16. |
| 3-35, 4-35, 5-35, 5-32, 7-32, 10-30, 12-28, 15-25, 17-23, 18-22 and ideally 19- | 10-35 |
| 3-35, 4-35, 5-35, 5-32, 7-32, 10-30, 12-28, 15-25, 17-23, 18-22 and ideally 19- 21. | 12-18 |
| ethanol and benzyl alcohol, most preferably each at about 10% | benzyl benzoate, most preferably at about 15% |

By the use of the term ricinoleate vehicle we mean an oil which has as a proportion (at least 20%, 30%, 40%, 50%, 60%, 70%, 80%, 90% or 95% w/v) of its composition as triglycerides of ricinoleic acid. The ricinoleate vehicle may be a synthetic oil or conveniently is castor oil, ideally of pharmacopoeial standards, as described above.

We have surprisingly found that the above formulations of the invention provide, after intra-muscular injection, satisfactory release of fulvestrant over an extended period of time.

This finding is indeed surprising for the following reasons.
1. Previously tested by the applicants have been intra-muscular injections of fulvestrant in the form of an aqueous suspension. We have found extensive local tissue irritation at the injection site as well as a poor release profile. It is believed that the tissue irritation/inflammation was due to the presence of fulvestrant in the form of solid particles.

The release profile appeared to be determined by the extent of inflammation/irritation present at the injection site and this was variable and difficult to control. Also the fulvestrant release rate was not sufficiently high to be clinically significant.

2. Our findings from studies using $^{14}C$ labelled benzyl alcohol show that it dissipates rapidly from the injection site and is removed from the body within 24 hours of administration.

It would be expected that ethanol will dissipate at least as quickly, if not more rapidly, from the injection site.

It is known that benzyl benzoate is metabolised by conjugation to glycine to form hippuric acid by the human liver and excreted into the urine—Martindale: The Extra Pharmacopoeia $32^{nd}$ edition page 1103, and, therefore, it is unlikely that benzyl benzoate, when used, is present at the injection site during the whole of the extended release period.

We have found that despite the rapid elimination of the additional solubilising excipients, i.e. the alcohol and pharmaceutically-acceptable non-aqueous ester solvent, from the formulation vehicle and the site of injection after injection of the formulation, extended release at therapeutically significant levels of fulvestrant over an extended period can still achieved by the formulation of the invention.

By use of the term "therapeutically significant levels" we mean that blood plasma concentrations of at least 2.5 ngml$^{-1}$, ideally at least 3 ngml$^{-1}$, at least 8.5 ngml$^{-1}$, and up to 12 ngml$^{-1}$ of fulvestrant are achieved in the patient. Preferably blood plasma levels should be less than 15 ngml$^{-1}$.

By use of the term "extended release" we mean at least two weeks, at least three weeks, and, preferably at least four weeks of continuous release of fulvestrant is achieved. In a preferred feature extended release is achieved for 36 days. Preferably extended release of fulvestrant is for at least 2-5 weeks and more preferably for the following periods (weeks) 2.5-5, 2.5-4, 3-4, 3.5-4 and most preferably for at least about 4 weeks.

It will be understood that the attendant physician may wish to administer the intramuscular injection as a divided dose, i.e. a 5 ml formulation is sequentially administered in two separate injections of 2.5 ml, this is a further feature of the invention Simply solubilising fulvestrant in an oil based liquid formulation is not predictive of a good release profile or lack of precipitation of drug after injection at the injection site.

Table 3 shows the solubility of fulvestrant in a castor oil vehicle additionally containing alcohols ethanol and benzyl alcohol with or without benzyl benzoate. The results clearly show the positive effect of benzyl benzoate on fulvestrant solubility in castor oil, despite fulvestrant having a lower solubility in benzyl benzoate than in either alcohol or castor oil.

TABLE 3

Table 3 - EFFECT OF BENZYL BENZOATE ON FULVESTRANT SOLUBILITY IN CASTOR OIL AT 25° C.

| | % w/v | | | | | | | |
|---|---|---|---|---|---|---|---|---|
| Ethanol (96%) | 5 | 5 | 10 | 10 | 10 | 10 | 15 | 15 |
| Benzyl Alcohol | 5 | 5 | 5 | 5 | 10 | 10 | 15 | 15 |
| Benzyl Benzoate | | 15 | | 15 | | 15 | | 15 |
| Castor Oil | to 100 | to 100 | to 100 | to 100 | to 100 | to 100 | to 100 | to 100 |
| Fulvestrant Solubility [mgml$^{-1}$] | 27 | 36 | 46 | 54 | 45 | 65 | 76 | 102 |

The following Table 4 shows the solubility of fulvestrant in a range of oil based formulations which contain the same amounts of alcohol and benzyl benzoate but in which the oil is changed. The data also shows solubility of fulvestrant after removal of the alcohols.

TABLE 4

Solubility comparisons of fulvestrant in oil based formulations with and without alcohols

| | Fulvestrant Solubility mg ml$^{-1}$ @ 25° C. | |
|---|---|---|
| Formulation [a] | Complete vehicle | Vehicle minus alcohols |
| Castor oil based | 81.2 | 12.6 |
| Miglyol 812-N based | 86.8 | 1.7 |
| Sesame seed/Castor oil (1:1) based | 70.1 | 4.4 |
| Sesame seed oil based | 45.7 | 0.7 |
| Arachis oil based | 40.2 | <0.2 |

[a] Complete Vehicle Formulations comprised ethanol [96%](10%), benzyl alcohol (10%) and benzyl benzoate (15%) made to volume with the stated oil. Excess fulvestrant was added to each solvent mixture and solubility determined.

Effect of Formulation on Precipitation of Fulvestrant at the Injection Site

| | Days | | | | | | |
|---|---|---|---|---|---|---|---|
| Formulation [a] | 2 | 3 | 4 | 7 | 10 | 30 | 51 |
| Formulation F1 castor oil based | 0 | 0 | 0 | 0 | 0 | 0 | 0 |
| Formulation F2 Miglyol 812-N based | ++ [b] | +++ | +++ | +++ | +++ | ++ | 0 |
| Formulation F3 sesame seed/ castor oil based | + [c] | ++ | ++ | +++ | ++ | + | + |

0, +, ++, +++ = Degree of precipitation (None detected, Mild, Moderate, Severe)
[a] Formulations comprised fulvestrant (5%), ethanol [96%] (10%), benzyl alcohol (10%) and benzyl benzoate (15%) made to volume with the stated oil.
[b] Mainly large needle shaped crystals
[c] Small needles and/or sheafs of crystals Precipitation of fulvestrant and the release profile was determined with the above formulations in an in vivo rabbit study.

FIG. 1 shows the release profile in vivo of the four formulations from the second part of Table 4 and shows the effect of the fixed oil component on fulvestrant plasma profile over five days following intramuscular administration in rabbits (data normalised to 50 mg per 3 kg; mean given; number of animals per timepoint=8, plasma samples assayed for fulvestrant content using lc-ms/ms detection following solvent extraction). As can be seen the castor oil formulation showed a particularly even release profile with no evidence of precipitation of fulvestrant at the injection site.

Therefore we present as a further feature of the invention an extended release pharmaceutical formulation adapted for intramuscular injection comprising fulvestrant; 35% (preferably 30% or ideally 25%) or less weight of a pharmaceutically-acceptable alcohol per volume of formulation, at least 1% (preferably at least 5% or ideally 10%) weight of a pharmaceutically-acceptable non-aqueous ester solvent miscible in a ricinoleate vehicle per volume of formulation and sufficient amount of a ricinoleate vehicle, taking into account the addition of any further optional pharmaceutically-acceptable excipients, so as to prepare a formulation of at least 45 mgml$^{-1}$ of fulvestrant.

A further feature of the invention is a pharmaceutical formulation adapted for intramuscular injection, as defined above, for use in medical therapy.

A further feature of the invention is a method of treating a benign or malignant diseases of the breast or reproductive tract, preferably treating breast cancer, by administration to a human in need of such treatment by intramuscular injection an extended release ricinoleate vehicle based pharmaceutical formulation comprising at least 45 mgml$^{-1}$ of fulvestrant; 35% (preferably 30% or ideally 25%) or less weight of a pharmaceutically-acceptable alcohol per volume of formulation, at least 1% (preferably at least 5% or ideally 10%) weight of a pharmaceutically-acceptable non-aqueous ester solvent miscible in a ricinoleate vehicle per volume of formulation.

Preferably 5 ml of the intramuscular injection is administered.

A further feature of the invention is use of fulvestrant in the preparation of a pharmaceutical formulation as describe hereinabove, for the treatment of a benign or malignant disease of the breast or reproductive tract, preferably treating breast cancer.

Additional excipients commonly used in the formulation field including, for example, an antioxidant preservative, a colorant or a surfactant may be used. A preferred optional excipient is a surfactant.

As described above fulvestrant is useful in the treatment of oestrogen-dependent indications such as breast cancer and gynaecological conditions, such as endometriosis.

In addition to fulvestrant another similar type of molecule is currently under clinical investigation. SH-646 (11β-fluoro-7α-(14,14,15,15,15-pentafluoro-6-methyl-10-thia-6-azapentadecyl)estra-1,3,5(10)-triene-3,17β-diol) is also putatively a compound with the same mode of action as fulvestrant and has a very similar chemical structure. It is believed that the compound will also share with fulvestrant similar physical properties and therefore the current invention will also have application with this compound.

A further feature of the invention is a pharmaceutical formulation adapted for intra-muscular injection comprising 11β-fluoro-7α-(14,14,15,15,15-pentafluoro-6-methyl-10-thia-6-azapentadecyl)estra-1,3,5(10)-triene-3,17β-diol; 35% or less weight of a pharmaceutically-acceptable alcohol per volume of formulation, at least 1% weight of a pharmaceutically-acceptable non-aqueous ester solvent miscible within a ricinoleate vehicle per volume of formulation and a sufficient amount of a ricinoleate vehicle so as to prepare a formulation of at least 45 mgml$^{-1}$ of 11β-fluoro-7α-(14,14,15,15,15-pentafluoro-6-methyl-10-thia-6-azapentadecyl)estra-1,3,5(10)-triene-3,17β-diol.

Further features of the invention are those as described above but in which SH-646 is substituted for fulvestrant.

FORMULATION EXAMPLE

Fulvestrant is mixed with alcohol and benzyl alcohol, stirring until completely dissolved. Benzyl benzoate is added and the solution is made to final weight with castor oil and stirred, (for convenience weight is used rather than volume by using the weight to volume ratio). The bulk solution is overlaid with Nitrogen. The solution is sterilised by filtration using one or two filters of 0.2 μm porosity. The sterile filtrate is kept under a nitrogen overlay as it is filled under aseptic conditions into washed and depyrogenised, sterile primary containers, for example vials or pre-filled syringes. An overage is included in the primary pack to facilitate removal of the dose volume. The primary packs are overlaid with sterile nitrogen, before aseptically sealing.

See also process flow diagram of FIG. 2.

Quantities of each component of the formulation is chosen according to the required formulation specification, examples are described above. For example quantities are added of each component to prepare a formulation which contains 10% weight per volume of benzyl alcohol
10% weight per volume of ethanol
15% weight per volume of benzyl benzoate
250 mg of fulvestrant for each 5 ml of finished formulation
and the remaining amount as castor oil

REFERENCES

1. Bowler J, Lilley T J, Pittam J D, Wakeling A E. Novel steroidal pure antioestrogens. Steroids 989; 5471-99.
2. Wakeling A E. Novel pure antioestrogens: mode of action and therapeutic prospects. American New York Academy Science 1990a; 595: 348-56.
3. Wakeling A E. Steroidal pure antioestrogens. In Lippman M, Dickson R, editors. Regulatory mechanisms in breast cancer. Boston: Kluwer Academic, 1990b: 239-57.
4. Wakeling A E. Therapeutic potential of pure antioestrogens in the treatment of breast cancer. Journal Steroid Biochemistry 1990c; 37: 771-5.
5. Wakeling A E, Bowler J. Steroidal pure antioestrogens. Journal Endocrinology 1987; 112: R7-10.
6. Wakeling A E, Bowler J. Biology and mode of action of pure antioestrogens. Journal Steroid Biochemistry 1988; 3: 141-7.

The invention claimed is:

1. A method for treating a hormonal dependent benign or malignant disease of the breast or reproductive tract comprising administering intramuscularly to a human in need of such treatment a formulation comprising:
about 50 mgml$^{-1}$ of fulvestrant;
about 10% w/v of ethanol;
about 10% w/v of benzyl alcohol;
about 15% w/v of benzyl benzoate; and
a sufficient amount of castor oil vehicle;
wherein the method achieves a therapeutically significant blood plasma fulvestrant concentration of at least 2.5 ngml$^{-1}$ for at least four weeks.

2. The method of claim 1, wherein the therapeutically significant blood plasma fulvestrant concentration is at least 8.5 ngml$^{-1}$.

3. The method of claim 1, wherein the hormonal dependent benign or malignant disease of the breast or reproductive tract is breast cancer.

4. The method of claim 1, wherein the method comprises administering intramuscularly to a human in need of such treatment 5 mL of the formulation.

5. The method of claim 1, wherein the method further comprises once monthly administration of the formulation.

6. The method of claim 2, wherein the hormonal dependent benign or malignant disease of the breast or reproductive tract is breast cancer.

7. The method of claim 6, wherein the method comprises administering intramuscularly to a human in need of such treatment 5 mL of the formulation.

8. The method of claim 7, wherein the method further comprises once monthly administration of the formulation.

9. A method for treating a hormonal dependent benign or malignant disease of the breast or reproductive tract comprising administering intramuscularly to a human in need of such treatment a formulation consisting essentially of:
- about 50 mgml$^{-1}$ of fulvestrant;
- about 10% w/v of ethanol;
- about 10% w/v of benzyl alcohol;
- about 15% w/v of benzyl benzoate; and
- wherein the method achieves a therapeutically significant blood plasma fulvestrant concentration of at least 2.5 ngml$^{-1}$ for at least four weeks.

10. The method of claim 9, wherein the therapeutically significant blood plasma fulvestrant concentration is at least 8.5 ngml$^{-1}$.

11. The method of claim 9, wherein the hormonal dependent benign or malignant disease of the breast or reproductive tract is breast cancer.

12. The method of claim 9, wherein the method comprises administering intramuscularly to a human in need of such treatment 5 mL of the formulation.

13. The method of claim 9, wherein the method further comprises once monthly administration of the formulation.

14. The method of claim 10, wherein the hormonal dependent benign or malignant disease of the breast or reproductive tract is breast cancer.

15. The method of claim 14, wherein the method comprises administering intramuscularly to a human in need of such treatment 5 mL of the formulation.

16. The method of claim 15, wherein the method further comprises once monthly administration of the formulation.

17. The method according to claim 1, wherein the formulation is administered in a divided dose.

18. The method according to claim 8, wherein the formulation is administered in a divided dose.

19. The method according to claim 9, wherein the formulation is administered in a divided dose.

20. The method according to claim 16, wherein the formulation is administered in a divided dose.

* * * * *